(12) United States Patent
Monteiro et al.

(10) Patent No.: US 7,892,538 B2
(45) Date of Patent: Feb. 22, 2011

(54) MONOVALENT LIGAND OF THE FCαRI RECEPTOR AS AN ANTI-INFLAMMATORY AGENT

(75) Inventors: Renato Monteiro, Montrouge (FR); Benoît Pasquier, Saint André de la Marche (FR); Ulrich Blank, Sartrouville (FR); Marc Benhamou, Paris (FR); Pierre Launay, Marnes la coquette (FR); Marina Pretolani, Paris (FR)

(73) Assignee: Institut National de la Sante Et de la Recherche, Paris (FR)

( * ) Notice: Subject to any disclaimer, the term of this patent is extended or adjusted under 35 U.S.C. 154(b) by 768 days.

(21) Appl. No.: 10/591,642

(22) PCT Filed: Mar. 4, 2005

(86) PCT No.: PCT/EP2005/002882

§ 371 (c)(1),
(2), (4) Date: Jul. 16, 2007

(87) PCT Pub. No.: WO2005/089798

PCT Pub. Date: Sep. 29, 2005

(65) Prior Publication Data

US 2008/0085280 A1 Apr. 10, 2008

(30) Foreign Application Priority Data

Mar. 5, 2004 (EP) .................................. 04290615

(51) Int. Cl.
*A61K 39/395* (2006.01)
(52) U.S. Cl. .............. 424/130.1; 424/139.1; 424/144.1; 424/804; 424/809; 514/12.2
(58) Field of Classification Search ....................... None
See application file for complete search history.

(56) References Cited

U.S. PATENT DOCUMENTS

| | | | |
|---|---|---|---|
| 6,018,031 A | 1/2000 | Shen et al. | |
| 2001/0014328 A1* | 8/2001 | Deo et al. | 424/136.1 |

FOREIGN PATENT DOCUMENTS

| | | |
|---|---|---|
| WO | 99/28349 | 6/1999 |
| WO | 99/41285 | 8/1999 |
| WO | 02/064634 | 8/2002 |
| WO | WO 02064634 A2 * | 8/2002 |

OTHER PUBLICATIONS

Buc et al., Arch Immunol Ther Exp (Warsz). Sep.-Oct. 2009;57(5):331-44. Epub Aug. 18, 2009.*
Kanamaru et al., J Immunol. Feb. 15, 2008;180(4):2669-78.*
Morton, H Craig et al., "CD89: the Human Myeloid IgA Fc Receptor," Archivum Immunolgiae et Therapiae Experimentalis, vol. 49, No. 3, 2001, pp. 217-229, XP009035083, PL ISSN: 0004-069X.
PCT International Search Report dated Jun. 6, 2006.

* cited by examiner

*Primary Examiner*—Michael Szperka
(74) *Attorney, Agent, or Firm*—William E. Beaumont

(57) ABSTRACT

The invention relates to the use of a monovalent antibody fragment directed against the EC2 domain of the FcαRI receptor for the treatment of inflammatory diseases.

14 Claims, 8 Drawing Sheets

SEQUENCE LISTING

<160> NUMBER OF SEQ ID NOS: 4

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gggctcgaga tggaccccaa acagaccacc                                        30

<210> SEQ ID NO 2
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctttcgcact tggatcttca gattttcaac cagtatggcc aa                          42

```
<210> SEQ ID NO 3
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ttggccatac tggttgaaaa tctgaagatc caagtgcgaa ag                         42

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gggggatcct tactgtggtg gtttctcatg                                       30
```

MONOVALENT LIGAND OF THE FCαRI RECEPTOR AS AN ANTI-INFLAMMATORY AGENT

BACKGROUND OF THE INVENTION

1. Field of the Invention

The invention relates to the use of a monovalent ligand of the FcαRI IgA receptor as an anti-inflammatory agent.

2. Description of the Background

Immunoglobulin A (IgA) is the most heterogeneous Ig isotype in humans, existing in multiple molecular forms such as monomeric, polymeric and secretory IgA; it comprises two subclasses IgA1 and IgA2.

In serum, IgA exists mainly in monomeric form, with a minor percentage of polymeric IgA (pIgA).

In mucosal secretions (saliva, tears, colostrum, gastrointestinal fluids, nasal bronchial secretion, and urine), IgA is produced as dimers, joined by a polypeptide termed J-chain. Dimeric IgA binds to the membrane-associated polymeric Ig receptor (pIgR), and the resulting complex is transported from the baso-lateral to the apical/luminal side of mucosal epithelium. During this transport the bound IgA is released by proteolytic cleavage from the pIgR; however a portion of the pIgR, the secretory component, remains associated with dimeric IgA, forming altogether secretory IgA (SIgA).

SIgA plays a major role in the innate immune system preventing microorganisms and foreign proteins from penetrating the mucosal surfaces. It also neutralizes toxins and infectious organisms.

Whereas the role of secretory IgA is established in mucosal immunology, the function of serum IgA antibodies is mostly unknown. Although IgA is the second most abundant Ig isotype in serum, it is not usually involved in humoral immune responses and does not activate complement. Monomeric serum IgA has anti-inflammatory activity and is capable of down-regulating functions such as IgG-induced phagocytosis, bactericidal activity, oxidative burst, and cytokine release. In contrast, polymeric IgA and IgA-containing immune complexes (IC) can efficiently trigger immune effector functions on blood leukocytes through IgA Fc receptors.

Receptors for the Fc region of immunoglobulins (FcRs) play a major part in the link between humoral and cellular responses. FcRs for all five human antibody classes have been described.

The human IgA Fc receptors (FcαR) family comprises several members (for review cf. MONTEIRO and VAN DE WINKEL, Annu. Rev. Immunol. 21: 177-204, 2003), but only FcαRI (or CD89), a receptor specific for the IgA Fc region, has been identified on blood myeloid cells (MONTEIRO and al., J. Exp. Med. 171: 597-613, 1990; MALISZEWSKI and al., J. Exp. Med. 172: 1665-1672, 1990). FcαRI is expressed on monocyte/macrophages, dendritic cells, Kupffer cells, neutrophils and eosiniphils and binds both IgA1 and IgA2 (CONLEY and DELACROIX, Ann. Int. Med. 106: 892-899, 1987; KERR, Annu. Rev. Immunol. 12: 63-84, 1994) with low affinity (Ka≈$10^6$ M$^{-1}$) (MONTEIRO and VAN DE WINKEL, 2003, aforementioned).

FcαRI is a member of the Ig gene superfamily. It comprises two extracellular Ig-like domains (EC1 and EC2), a transmembrane region and a cytoplasmic tail devoid of recognized signaling motifs. Crystal structures of human FcαRI reveal that the two Ig-like domains are oriented at right angles to each other and that two FcαRI molecules are required for the binding of one IgA molecule (HERR and al., J. Mol. Biol. 327: 645-657, 2003). The IgA binding site is located in the membrane-distal EC1 domain. Anti-FcαRI mouse and human monoclonal antibodies (mAb) have been generated (MONTEIRO and al., J. Immunol. 148: 1764-1770, 1992; SHEN et al., J. Immunol. 143, 4117-4122, 1989; PCT WO 91/05805; PCT WO 02/064634), and it has been shown that monoclonal antibodies that bind in the EC1 domain of FcαRI block IgA binding, whereas those that bind in EC2 do not.

Due to the moderately fast on- and off-rates of the FcαRI: IgA binding reaction, monomeric IgA binding is transient, whereas polymeric IgA and IgA immune complexes bind with a respectively growing avidity due to a decrease in the off-rate (HERR and al., 2003, aforementioned; WINES, J. Immunol. 162: 2146-2153, 1999).

The involvement of FcαRI in the ability of IgA to trigger immune responses such as phagocytosis, antibody-dependent cell-mediated cytotoxicity (ADCC), superoxide generation, cytokine production, antigen presentation and inflammatory mediator release, has been reported (for review, see MONTEIRO and VAN DE WINKEL, 2003, aforementioned). It has been proposed to use anti-FcαRI antibodies, such as My 43 (PCT WO 91/05805), or the human monoclonal antibodies disclosed in PCT WO 02/064634, to activate these FcαRI-mediated immune responses.

It has also been proposed to use anti-FcR antibodies, including anti-FcαRI antibodies, as vectors for selectively targeting active principles, such as cytotoxic compounds, to cells expressing Fc receptors (PCT WO 99/41285).

U.S. Pat. No. 6,018,031 describes bifunctional antibodies containing the binding region of an anti-FcαR antibody and the binding region of an antibody directed against a target cell. These bifunctional antibodies can bind on one hand said target cell, and on the other hand effector cells expressing FcαR. Their binding to FcαR triggers the FcαR-mediated activity of the effector cell, resulting in the destruction of the target cell bound to the same bifunctional antibody molecule.

Signaling through FcαRI is dependent on association of FcαRI with the FcRγ chain subunit, forming the trimer FcαRIα/γγ. The FcRγ chain contains an immunoreceptor tyrosine-based activation motif (ITAM) in its cytoplasmic tail (PFEFFERKORN and YEAMAN, J. Immunol. 153: 3228-3236, 1994; LAUNAY and al., J. Biol. Chem. 274: 7216-7225, 1999) that allows the recruitment of crucial signalling effectors (KINET, Annu. Rev. Immunol. 17: 931-972, 1999). FcαRI can be expressed with or without physical association with FcRγ subunit. The γ-less FcαRI internalises and recycles IgA to the cell surface, whereas FcRγ-associated FcαI directs complexed IgA to lysosomes (LAUNAY and al., 1999, aforementioned; SHEN and al., Blood 97: 205-213, 2001). No cellular function of non aggregated FcαRI, other than IgA recycling, has so far been identified. Receptor aggregation is required for FcαRI-mediated activation of target cell functions such as cytokine release and antigen presentation (SHEN and al., 2001, aforementioned; PATRY and al., Immunol. 86: 1-5, 1995; GEISSMANN and al., J. Immunol. 166: 346-352, 2001).

While involvement of FcαRI in IgA-mediated inflammation is well recognized, the molecular basis that underlies the IgA anti-inflammatory capacity has not been elucidated until now. Although it has been reported (WILTON, Clin. Exp. Immunol. 34, 423-8 1978; VAN EPPS and WILLIAMS, J Exp Med 144, 1227-42 1976) that IgA inhibitory functions require the Fcα region, the part played by IgA Fc receptors remains unknown.

A consensus model of negative signaling in the immune system involves receptors with an immunoreceptor tyrosine-based inhibitory motif (ITIM) in their cytoplasmic domain. These inhibitory receptors act by co-aggregating with activatory receptors: cross-talk between the two receptors generates a negative signal (RAVETCH and LANIER, Science, 290, 84-89, 2000). An example of the ITIM class of inhibitory receptors is the Fcγ receptor FcγRIIB. However no ITIM receptor for the Fcα region is known.

SUMMARY OF THE INVENTIOIN

The Inventors now found that unexpectedly, monomeric occupancy of FcαRI by a monovalent Fab fragment of an antibody directed against the EC2 domain of FcαRI strongly inhibited IgG-induced phagocytosis and IgE-mediated exocytosis, in vitro, and that, surprisingly, these effects were mediated by the ITAM motif of the FcαRI-associated FcRγ subunit.

Further, the Inventors have shown in an asthma model, that in vivo targeting of FcαRI by said monovalent Fab fragment abolished antigen-induced bronchial hyper-reactivity and the accompanying airway inflammation particularly leukocyte infiltration into the lung tissue. They have also shown in a model of interstitial renal fibrosis and obstructive nephropathy, that in vivo targeting of FcαRI by said monovalent Fab fragment considerably decreased the pathological inflammatory reactions.

An object of the present invention is the use of a monovalent antibody fragment directed against the EC2 domain of the FcαRI receptor, as anti-inflammatory active principle in the preparation of a medicament for treating an inflammatory disease.

BRIEF DESCRIPTION OF THE DRAWINGS

FIG. 6 (c) illustrates that anti-FcaRI Fab A77 treatment had no effect on EGTA-treated cells indicating that it did not inhibit the release of intracellular calcium stores. The legend for this figure is described at Example 5, section 3).

FIGS. 6 (d-f) illustrate that addition of $Mn^{2+}$ decreased fluorescence, owing spontaneous entry of $Mn^{2+}$ ions into cells. FccRI stimulation induced a further significant decrease in fluorescence as a consequence of $Mn^{2+}$ influx through opened SOC (FIG. 6(d)). Cell incubation with anti-FcαRI A77 prior to IgE-dependent stimulation abrogated this effect (FIG. 6(e)), while an irrelevant Fab 320 was ineffective (FIG. 6(f)). The legend for these figures is described in Example 5, section 4.

FIGS. 6 (g, h) illustrate that thapsigargin-induced sustained $[Ca^{2+}]$ i elevation was markedly reduced by preincubation with anti-FcaRI Fab A77 in FcaRI-transfected cells, as compared to irrelevant Fab 320 or untransfecte cells (FIG. 6 (h)). The legend for these figures are described in Example 5, section 5).

FIGS. 7 (*c-k*) illustrate the pulmonary histology of antigen-challenged Tg mice treated with the irrelevant Fab 320, which showed peribronchial (FIG. 7(*f*)) and epithelial (FIG. 7(*g*)) inflammatory infiltrates consisting mainly of granulocytes and mononuclear cells, and diffuse alveolar capillary congestion (FIG. 7(*h*)) (see arrows). These features were absent in lungs from PBS-challenged mice (FIG. 7 (*c-e*)) showing normal physiology. Antigen-challenged anti-FcαRI Fab A77-treated mice showed substantially less inflammation and congestion (FIG. 7 (*i-k*)). Anti-FcαRI Fab administration prevented antigen-induced airway congestion and infiltration by inflammatory cells. The legend for these figures is described in Example 6.

DETAILED DESCRIPTION OF THE PREFERRED EMBODIMENT

Figure 1:
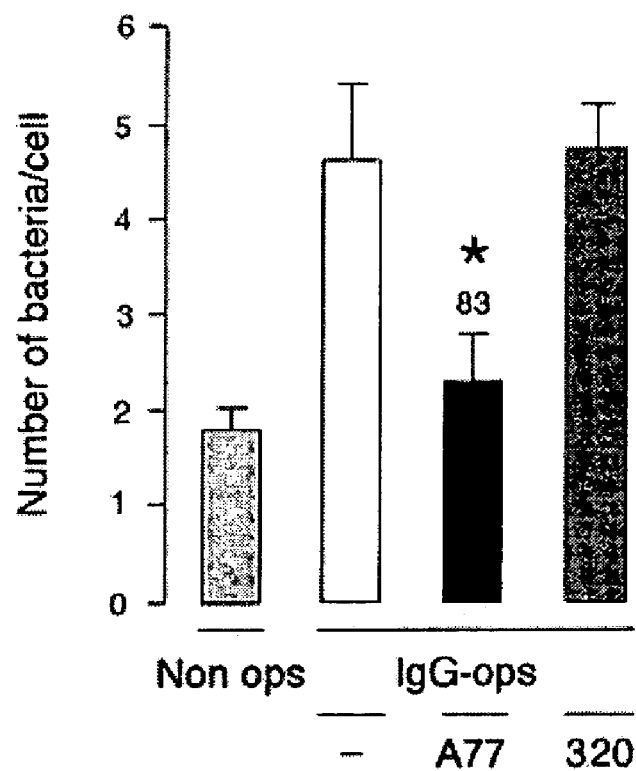
FIG. 1 illustrates mean number of ingested bacteria per monocyte in six experiments with different healthy donors. The number above the bar corresponds to the mean percentage of inhibition by Fab. The legend for the figure is described in Example 1.

The anti-inflammatory properties of said monovalent antibody fragment result from a down-regulation of the pathological inflammatory reactions involving FcαRI-expressing myeloid cells.

Examples of inflammatory diseases that can be treated according to the invention include allergic diseases in particular asthma, as well as inflammatory diseases involving interactions between immunoglobulins and FcR, such as nephritis, rheumatoid arthritis and auto-immune diseases (lupus, diabetes, etc). They also include non-immune inflammatory diseases such as those induced by unilateral ureteral obstruction resulting in kidney inflammation, drug induced toxicity of the kidney, gut inflammatory disorders such as Crohn's disease.

A monovalent antibody fragment is an immunoglobulin fragment that has only one antigen-binding site, in contrast with a whole immunoglobulin molecule, that comprises at least two antigen-binding sites. Examples of monovalent fragments are Fab fragments that consist of the light chain and the first half of the heavy chain, or scFv fragments that consist of the variable portions of the heavy and light chains of an antibody, connected to one another via a flexible linker (CLACKSON et al., Nature, 352, 624-628, 1991), thus forming a single-chain protein.

Methods allowing to obtain monovalent antibody fragments that can be used in the practice of the invention are well known in themselves.

By way of example, Fab fragments can be obtained, by the conventional techniques of enzyme digestion, from an antibody directed against the EC2 domain of the FcαRI receptor. Said antibody can be a murine monoclonal antibody obtained by the conventional hybridoma technology. Advantageously, it can also be a chimeric antibody, a humanized antibody, or a completely human antibody. Chimeric antibodies can be obtained from said monoclonal antibodies by replacing the constant-region domains by human domains; humanized antibodies can be obtained by incorporating the CDRs of said monoclonal antibodies into the framework regions (FRs) of a human antibody, using techniques, known in themselves, of CDR grafting. Completely human monoclonal antibodies can be obtained in the same way as conventional murine monoclonal antibodies, except that the mice immunized are transgenic mice with a human immunoglobulin repertoire, as disclosed for instance in PCT WO 02/064634.

Monovalent antibody fragments, in particular scFv fragments, can be directly obtained by expressing, in an appropriate host cell, a recombinant DNA comprising the DNA sequences encoding the variable regions of a monoclonal, humanized or human antibody directed against the EC2 domain of the FcαRI receptor, associated with an appropriate linker. They can also be generated from an antibody phage display library, panned with the EC2 domain of the FcαRI receptor. Humanized scFv fragments can also be obtained by the method described by ARNDT et al, (Int J Cancer 107, 822-829, 2003).

The specificity towards the EC2 domain of the FcαRI receptor of the above antibodies and monovalent fragments can be checked by testing their effect on the binding of IgA to the FcαRI receptor; the antibodies or fragments that do not block said binding are in most of cases directed against the EC2 domain. However, some non-blocking antibodies such as the monoclonal antibody A3, have been reported to recognize an epitope between EC1 and EC2 domains (MORTON et al., J Exp Med, 189, 1715-22, 1999). Accordingly, the above test will advantageously be completed or replaced by an assay of the binding of said antibodies or monovalent fragments to a recombinant protein comprising the EC2 domain and devoid of the EC1 domain of the FcαRI receptor, such as the chimeric receptor composed of FcαRI EC2 and bovine Fcγ2R EC1 described by MORTON et al. (1999, cited above). Alternatively, the monovalent fragments of anti-FcαRI antibodies that do not block the binding of IgA to the FcαRI receptor can directly be tested in vitro for their anti-inflammatory properties, for instance their ability to inhibit IgG-mediated phagocytosis in human blood monocytes, or to inhibit the IgE-mediated degranulation response of a mast-cell line expressing FcαRI, as described in the examples below.

For the practice of the invention, the monovalent antibody fragments can be administered, systemically or locally, in various ways.

By way of example they can be administered by the parenteral route, including for instance intramuscular, intradermal, intravenous, intraperitoneal, subcutaneous, or local injections.

Local administration in the respiratory tract can also be used, provided that the monovalent antibody fragments of the invention are in a form suitable for delivery to mucosal surfaces of the airways. For example, they may be suspended in a liquid formulation for delivery to a patient in an aerosol form or by means of a nebuliser device similar to those currently employed in the treatment of asthma.

The monovalent antibody fragments can be optionally mixed with suitable carriers and/or excipient(s) known to those of ordinary skill in the art.

The present invention will be understood more clearly from the further description which follows, which refers to non-limiting examples of preparation and of use of monovalent antibody fragments of anti-FcαRI antibodies in accordance with the invention.

EXAMPLE 1

FcαRI Targeting Inhibits IgG-Mediated Phagocytosis in Human Blood Monocytes In Vitro The role of FcαRI in the modulation of IgG-mediated phagocytic activity of blood monocytes was examined.

Human peripheral blood mononuclear cells were isolated by Ficoll-Hypaque density gradient centrifugation from healthy volunteers. Enriched (70 to 80%) monocyte populations were obtained by adherence to plastic as described in MONTEIRO and al. (1990, aforementioned).

Fab fragments of an anti-FcαRI mAb (IgG1κ, clone A77, MONTEIRO and al., J. Immunol. 148: 1764-1770, 1992) and of an irrelevant control monoclonal antibody (IgG1κ, clone 320) (PASTORELLI and al., J. Biol. Chem. 276: 20407-20412, 2001) were generated by pepsin digestion for 8 h at 37° C. followed by reduction with 0.01 M cysteine and alkylation with 0.15 M iodoacetamine at pH 7.5. Complete digestion and purity were controlled by SDS-PAGE.

Adherent blood mononuclear cells were preincubated with 10 μg/ml Fab A77 (c), irrelevant Fab 320 or buffer for 30 min at 37° C. After washing, cells were incubated at 37° C. for 30 min with Texas-red-conjugated $E.$ $coli$ (50 bacterial/cell) (Molecular Probes, Eugène, Oreg.), opsonized or not with polyclonal rabbit anti-$E.$ $coli$ IgG antibodies (Molecular Probes) according to the manufacturer's instructions. After washing, slides were mounted and examined with a confocal laser microscope (LSM 510 Carl Zeiss, Jena, Germany). Overlaid transmission and fluorescence images (mid sections) are shown. The panels (a-d) are representative of six independent experiments. The mean number (±SD) of ingested bacteria per monocyte in six experiments with different healthy donors is shown in FIG. 1. It was determined by counting at least three fields in each experiment. The number above the bar corresponds to the mean percentage of inhibition by Fab, calculated as follows: 100−100×(n of IgG-opsonized bacteria in the presence of Fab A77−n of non opsonized bacteria)/(n of IgG opsonized bacteria−n of non opsonized bacteria) in which n indicates the mean number of internalised bacteria.

The results are shown in FIG. 1.
Legend of FIG. 1:
Non opsonized bacteria (Non ops)
□=buffer
IgG opsonized bacteria (IgG-ops)
□=buffer
■=anti-FcαRI Fab A77
▨=irrelevant Fab 320
* $P<0.02$, Student's unpaired t test The results show that IgG opsonization enhanced $E.$ $coli$ phagocytosis by monocytes. Preincubation with anti-FcαRI Fab A77 fragment inhibited IgG-mediated phagocytosis by more 80% compared to the irrelevant Fab 320 fragment.

EXAMPLE 2

Characterization of FcαRI Inhibitory Function

The inhibitory function of FCαRI was further studied by testing the degranulation response of the rat mast-cell line RBL-2H3 that constitutively expresses the high-affinity receptor IgE (FcεRI), transfected with wild-type human FcαRI.

1) Material and Methods:

Cell Transfection:

Transfection of RBL-2H3 cells was performed as described by LAUNAY and al. (1999, aforementioned): the wild-type human FcαRI construct was cloned into pSRα-NEO vector containing a resistance gene to neomycin between XbaI-BamHI restriction sites and the sequence was controlled by DNA sequencing. RBL-2H3 cells, maintained as described by ROA and al. (J. Immunol. 159: 2815-2823, 1997), were transfected with 15 μg of DNA by electroporation at 250 V and 1500 μFa using an Easyjet+ apparatus (Eurogenetec, Seraing, Belgium).

Clones resistant for 1 mg/ml G418 were selected for FcαRI expression by flow cytometry. Cells were preincubated with 100 μg human polyclonal IgG (PharMingen, San Diego, Calif.) to block FcγRs before incubation with phycoerythrin-labeled anti-FcαRI mAb (IgG1κ, A59-PE) (MONTEIRO and al., 1992, aforementioned) or with an isotype-matched irrelevant Ab (Becton Dickinson, Bedford, Mass.). After washing, cells were analysed using a FACScalibur flow cytometer and CellQuest software (Becton Dickinson). One clone expressing human FcαRI (clone 15.4) was selected for the following experimentations.

Degranulation Response

Exocytosis of granular mediators contained in cells was determined by measuring the release of β-hexosaminisase as described in (ROA and al., 1997, aforementioned), by FcαRI transfected cells, or by non transfected cells used as a control, upon sensitization with different test reagents.

Cells were plated in 96-well plates (Becton Dickinson) at $5 \times 10^4$ cells/well. Cells were sensitized with different test reagents as hereafter indicated for each reagent. Cells were washed in prewarmed Tyrode buffer (135 mM NaCl, 5 mM KCl, 5.6 mM glucose, 10 mM HEPES, pH 7.3, 1.8 mM CaCl$_2$, 1 mM MgCl$_2$, and 5% BSA), and degranulation was triggered with 0.1 μg/ml DNP-HAS (Sigma). Net β-hexosaminidase release was calculated as a percentage of total content after subtracting spontaneous release.

2) Inhibition of IgE-mediated Exocytosis by anti-FcαRI Fab Fragments

Human FcαRI transfectants (clone 15.4) and non transfected (NT) RBL cells were sensitized with IgE anti-DNP (1:200) or IgE anti-DNP plus 10 μg/ml irrelevant Fab 320 control or anti-FcαRI Fab A77 for 1 h at 37° C. Cells were washed, degranulation was triggered with DNP-HSA, and β-hexosaminidase release was determined.

Figure 2:
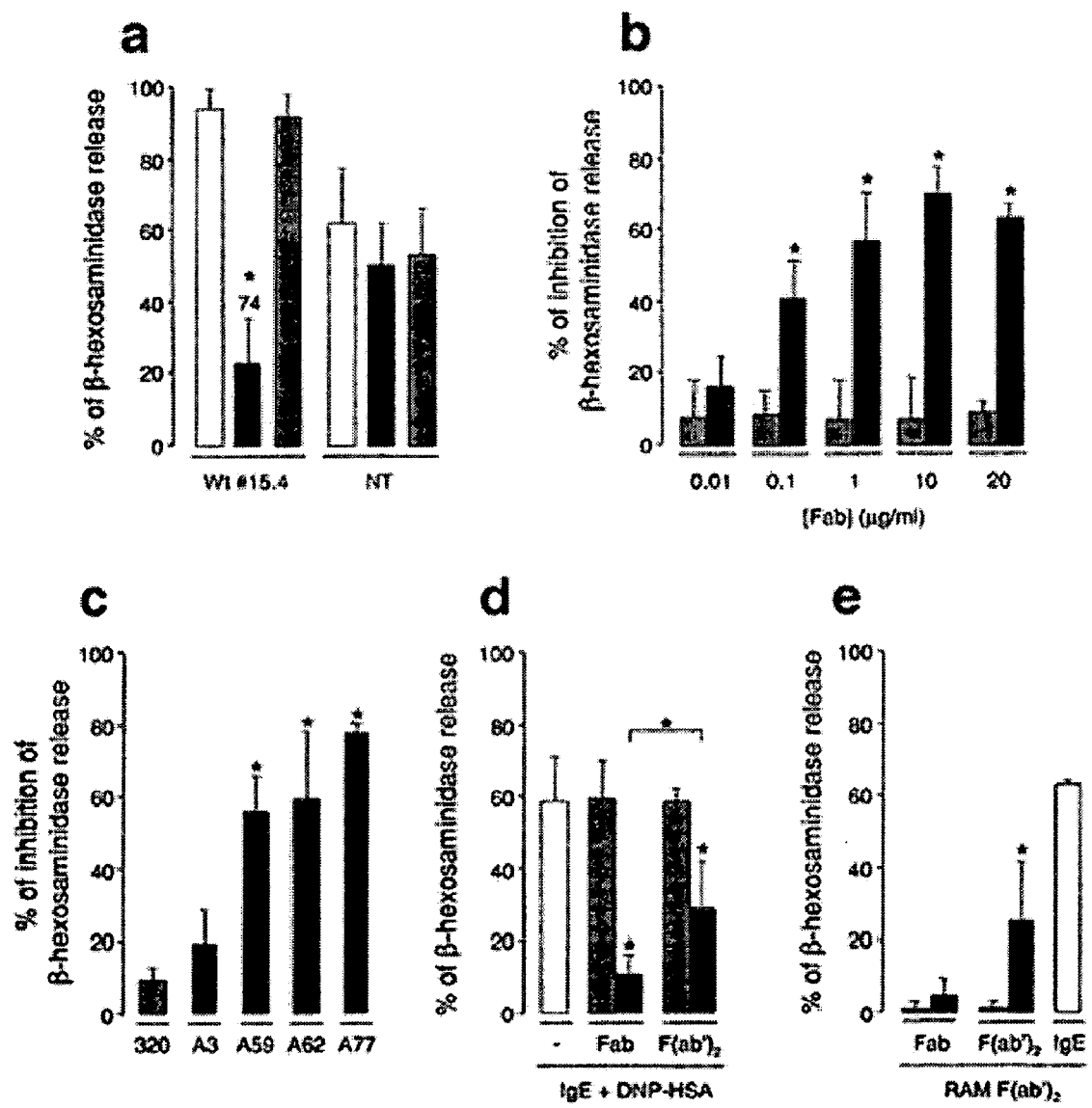
FIG. 2(a) illustrates mean percentage of degranulation in five experiments. The results show that antigen stimulation of IgE-sensitized transfectants induced a strong degranulation response. The legend for this figure is described in Example 2, section 2).
FIG. 2(b) illustrates data for four experiments showing that inhibition by anti-FcaRI-initiated degranulation Fab was concentration-dependent, and was maximal between 1 and 10 μg/ml. The legend for this figure is described in Example 2, section 3).
FIG. 2(c) illustrates data for three experiments showing that three of the four anti-FcaRI Fab tested inhibited FcαRI-induced degranulation by >50%, while the fourth failed to inhibit degranulation. The legend for this figure is described in Example 2, section 4).
FIG. 2(d) illustrates data for four experiments showing that monovalent anti-FcaRI Fab had a stronger inhibitory effect than the divalent F(ab')$_2$ fragments. The legend for this figure is described in Example 2, section 5).
FIG. 2(e) illustrates data for four experiments showing that highly multivalent aggregation of FcαRI, after crosslinking of anti-FcaRI F(ab')$_2$ with rabbit anit-mouse Ig (RAM) F(ab')$_2$, resulted in degranulation. The legend for this figure is described in Example 2, section 6).

The results are shown in FIG. 2a.
Legend of FIG. 2a:
Wt #15.4=human FcαRI transfectants (clone 15.4)
NT=non transfected RBL cells
□=IgE
■=IgE+A77 anti-FcαRI Fab
▨=IgE+irrelevant Fab 320
* $P<0.02$, Student's unpaired t test Data are means ±SD of five independent experiments. The number above the bar corresponds to the mean percentage inhibition of degranulation.

The results show that antigen stimulation of IgE-sensitized transfectants (clone 15.4) induced a strong degranulation response. Preincubation with anti-FcαRI Fab A77 markedly inhibited FcαRI-initiated degranulation (74%), as compared to an irrelevant Fab 320. Similar results were obtained with two others transfectants (not shown) but not with non transfected cells (NT). The inhibitory effect of A77 Fab was even stronger when preincubated for longer periods of time (2 to 12 hours) (not shown).

Of note, anti-FcαRI Fab failed to modify IgE binding (not shown). Anti-FcαRI Fab purified by gel filtration had a similar inhibitory action, ruling out a role of aggregates in the observed effects (not shown).

3) Dose Response Study of Anti-FcαRI Fab-mediated Inhibition

Human FcαRI transfectants (clone 15.4) were sensitized with IgE in the presence of different concentrations of anti-FcαRI Fab A77 of irrelevant Fab 320 for 1 h at 37° C. Cells were washed, degranulation was triggered with DNP-HSA, and β-hexosaminidase release was determined.

The results are show in FIG. 2b.

Legend of FIG. 2b:
■=IgE+anti-FcαRI Fab A77
☒=IgE+irrelevant Fab 320
* P<0.02, Student's unpaired t test.

Data are means ±SD of four independent experiments.

The results show that inhibition by anti-FcαRI Fab was concentration-dependent, and was maximal between 1 and 10 µg/ml.

4) Influence of Epitope Targeted by Anti-FcαRI Fab on Inhibition

Human FcαRI transfectants (clone 15.4) were sensitized with IgE in the presence of 10 µg/ml Fab fragment from different anti-FcαRI mAbs: A3 (recognizing a binding site between EC1 and EC2; A59, A62, A77, recognizing a binding site within EC2) or irrelevant Fab 320 for 1 h at 37° C.

Cells were washed, degranulation was triggered with DNP-HSA, and β-hexosaminidase release was determined.

The results are shown in FIG. 2c.

Legend of FIG. 2c:
■=anti-FcαRI Fab (A3, A59, A62, A77)
☒=irrelevant Fab 320
* P<0.01, Student's unpaired t test Data are means ±SD of three independent experiments.

Three of the four anti-FcαRI Fab tested inhibited FcεRI-induced degranulation by >50%. The fourth anti-FcαRI Fab (A3) failed to inhibit degranulation, even though, like its three counterparts, it bound readily to FcαRI-transfected cells (not shown).

5) Influence of Ligand Valence on Inhibition

For this purpose, F(ab')₂ were generated from the anti-FcαRI mAb (A77) or from the irrelevant antibody 320, by pepsin digestion for 8 h at 37° C. with an enzyme to substrate ratio (w/w) of 1/50 in 0.1 M acetate buffer, pH. 4.4 as described in SILVAIN and al. (J. Immunol. 155: 1606-1618, 1995). Complete digestion and purity were controlled by SDS-PAGE.

Human FcαRI transfectants (clone 15.4) were sensitized with IgE, or IgE plus 10 µg/ml Fab or F(ab')₂ fragments from A77, or IgE plus irrelevant Fab or F(ab')₂ fragments from 320, for 1 h at 37° C.

Cells were washed, degranulation was triggered with DNP-HSA, and β-hexosaminidase release was determined.

The results are shown in FIG. 2d.

Legend of FIG. 2d:
☐=IgE
■IgE+A77 Fab or F(ab')₂
☒=IgE+320 Fab or F(ab')₂
* P<0.01, Student's unpaired t test Data are means ±SD of four independent experiments.

The results show that monovalent anti-FcαRI Fab had a stronger inhibitory effect that the divalent F(ab')₂ fragments.

6) Influence of FcαRI Aggregation on Cell Degranulation

Human FcαRI transfectants (clone 15.4) were sensitized with IgE, or 10 µg/ml Fab or F(ab')₂ fragments from A77, or irrelevant Fab or F(ab')₂ fragments from 320, for 1 h at 37° C.

Cells were then stimulated with F(ab')₂ fragments of rabbit anti-mouse IgG (RAM at 40 µg/ml) (LAUNAY and al., J. Leukoc. Biol. 63: 636-642, 1998).

Cells were washed and β-hexosaminidase release was determined.

The results are shown in FIG. 2e.

Legend of FIG. 2e:
☐=IgE
■=A77 Fab or F(ab')₂
☒=320 Fab or F(ab')₂
* P<0.02, Student's unpaired t test Data are means ±SD of four independent experiments.

The results show that highly multivalent aggregation of FcαRI, after crosslinking of anti-FcαRI F(ab')₂ with rabbit anti-mouse Ig (RAM) F(ab')₂, resulted in degranulation. Less extensive multivalent aggregation with anti-FcαRI Fab plus RAM F(ab')₂ resulted in weaker degranulation. No degranulation was observed with anti-FcαRI Fab, F(ab')₂ or with RAM F(ab')₂ alone (not shown).

EXAMPLE 3

Serum IgA Induces FcαRI Inhibitory Function

The effect of the physiological ligand IgA was tested on FcαRI RBL-2H3 transfectants (clone 15.4), by testing the degranulation response, as described in Example 2 above.

1) Influence of Proteolytic Treatment on FcαRI Inhibitory Response to IgA

As IgA exert biological activity at inflammatory sites, which contain numerous mediators including proteases, the effect of trypsin treatment of cells on IgA-mediated inhibitory function was examined, given that FcαRI is resistant to trypsin (MONTEIRO and al., 1990, aforementioned).

Human FcαRI transfectants were pretreated or not with 1 mg/ml trypsin-TCPK (Sigma) in DMEM for 30 min at 37° C. and then sensitized overnight with IgE alone, or with IgE plus 0.2 mg/ml serum IgG, or purified serum IgA (batches n°39328 and 02828, ICN Biomedicals Inc, Aurora, Ohio).

Cells were washed, degranulation was triggered with DNP-HSA, and β-hexosaminidase release was determined.

Figure 3:
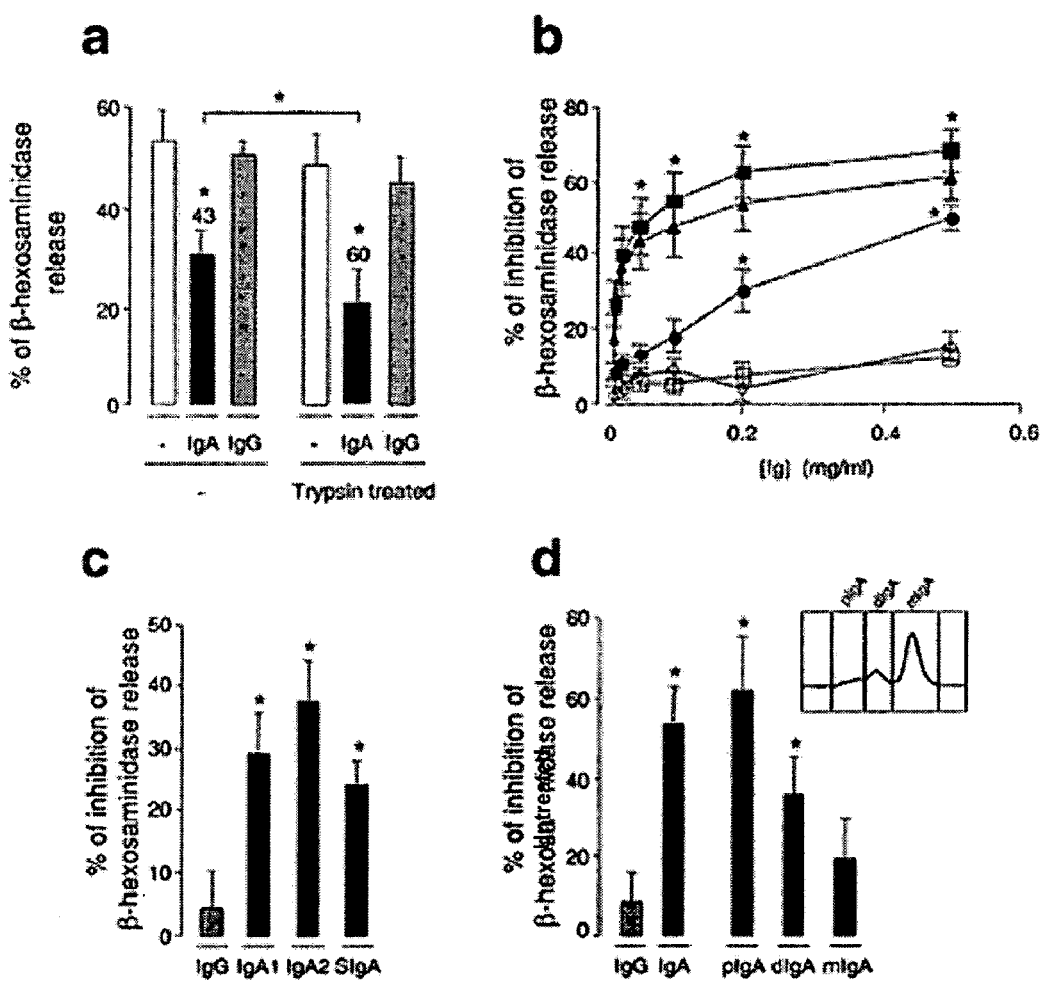
FIG. 3(a) illustrates data for six experiments showing that incubation with serum IgA, but not IgG, significantly inhibited IgE-dependent degranulation. The number above the bars indicate the mean percentage of inhibition. The legend for this figure is described in Example 3, section 1).
FIG. 3(b) illustrates data for five experiments showing that two different batches of commercial serum IgA inhibited degranulation in a dose-dependent manner with maximal inhibition (66%) being obtained at 0.5 mg/ml. The legend for this figure is described at Example 3, section 2) .
FIG. 3(c) illustrates data for four experiments showing that all tested preparations produced significant inhibition (30-40%) relative to human IgG (<5%). The FcaRI inhibitory response can be induced by both IgA1 and IgA2. The legend for this figure is described at Example 3, section 3).
FIG. 3(d) illustrates data for three experiments showing that polymeric serum IgA is more inhibitory than monomeric serum IgA. Inhibitory potency increased with the size of the IgA species. The legend for this figure is described at Example 3, section 4).

The results are shown in FIG. 3a.

Legend of FIG. 3a:
☐=IgE
■=IgE+serum IgA
☒=IgE+serum IgG
* P<0.01, Student's unpaired t test Data are means ±SD of six independent experiments.

Numbers above the bars indicate the mean percentage of inhibition.

The results show that incubation with serum IgA, but not IgG, significantly inhibited IgE-dependent degranulation (43%). The inhibitory effect of serum IgA, but not that of IgG, was significantly enhanced (~50% enhancement) in trypsin-treated cells, while the IgE-mediated degranulation response was not affected. A similar enhancement was observed with purified myeloma IgA (not shown).

2) Influence of Ig Concentration on FcαRI Inhibitory Function

Human FcαRI transfectants were pretreated with 1 mg/ml trypsin-TCPK (Sigma) in DMEM for 30 min at 37° C. and sensitized overnight with IgE alone or with IgE plus various concentrations of two batches of purified serum IgA (batches n°39328 and n°02828, ICN Biomedicals Inc, Aurora, Ohio), secretory IgA (SIgA, batch n°42K3780, Sigma Aldrich, St-Louis, Mo.) or human IgG.

Cells were washed, degranulation was triggered with DNP-HSA, and β-hexosaminidase release was determined.

The results are shown in FIG. 3b.

Legend of FIG. 3b:
◇=IgE
■=IgE+serum IgA (batch n°39328)
▲=IgE+serum IgA (batch n°02828)

●=IgE+SIgA
□=IgE+IgG
* P<0.01, Student's unpaired t test
Data are means ±SD of five independent experiments.

The results show that the two different batches of commercial serum IgA inhibited degranulation in a dose-dependent manner, maximal inhibition (66%) being obtained at 0.5 mg/ml. Colostral SIgA also inhibited cell activation, albeit to a somewhat lesser extent.

3) Modulation of FcαRI Inhibitory Response by IgA1 and IgA2

As FcαRI binds both IgA1 and IgA2, the inhibitory capacity of the two subclasses was compared relative to that of SIgA which contains variable amounts of both IgA1 and IgA2 depending on the type of secretory mucosa.

Human FcαRI transfectants were pretreated with 1 mg/ml trypsin-TCPK (Sigma) in DMEM for 30 min at 37° C. and sensitized overnight with IgE plus 0.2 mg/ml serum IgG, purified myeloma IgA1 and IgA2 or SIgA. Cells were washed, degranulation was triggered with DNP-HSA, and β-hexosaminidase release was determined.

The results are shown in FIG. 3c.
Legend of FIG. 3c:
▨=IgG
■=IgA1, IgA2 or SIgA
* P<0.02, Student's unpaired t test
Data are means ±SD of four independent experiments.

The results show that all tested preparations produced significant inhibition (30-40%) relative to human IgG (<5%). The FcαRI inhibitory response can be induced by both IgA1 and IgA2.

4) Comparison of Polymeric and Monomeric Serum IgA Inhibition

As FcαRI binds polymeric IgA more efficiently than monomeric IgA, the inhibitory potential of the various molecular forms of IgA (separated by HPLC), without secondary crosslinking was examined.

Human FcαRI transfectants were pretreated with 1 mg/ml trypsin-TCPK (Sigma) in DMEM for 30 min at 37° C. and sensitized overnight with IgE plus 0.1 mg/ml serum IgG (IgG), total serum IgA (IgA), polymeric serum IgA (pIgA), dimeric serum IgA (dIgA) or monomeric serum IgA (mIgA). Serum IgA was size-fractionated by HPLC.

Cells were washed, degranulation was triggered with DNP-HSA, and β-hexosaminidase release was determined.

The results are shown in FIG. 3d.
Legend of FIG. 3d:
▨=IgG
■=IgA, pIgA, dIgA or mIgA
inset=size-fractionated serum IgA by HPLC
* P<0.02, Student's unpaired t test
Data are means ±SD of three independent experiments.

The results show that polymeric serum IgA is more inhibitory than monomeric serum IgA. Inhibitory potency increased with the size of the IgA species: polymeric IgA were more efficient (60%) than both dimeric IgA (38%) and monomeric IgA (20%). Similar data were obtained with a different batch of serum IgA separated by HPLC (not shown).

The difference between A77 mAb and IgA may be explained by the binding site and the ligand avidity. While anti-FcαRI mAb A77 biding site is localized in EC2, IgA interacts with EC1 domain (MORTON and al., J. Exp. Med. 189: 1715-1722, 1999) and polymeric IgA bind more avidly to FcαRI than monomeric IgA (HERR and al., 2003, aforementioned; WINES and al., 1999, aforementioned). No β-hexosaminidase release was observed when the different IgA preparations were incubated alone with transfected RBL-2H3 cells, and IgE-mediated degranulation was not inhibited in non transfected cells (NT) (not shown).

EXAMPLE 4

The FcαRI Inhibitory Signal is Mediated by the ITAM Motif of the FcRγ Chain

To explore the structural requirements for the inhibitory signal, a series of FcαRI mutants and chimeric constructs was used:

FcαRI$_{R209L}$ wherein the charged arginine at position 209, within the FcαRI transmembrane domain, is replaced by a leucine (R209L); this mutation abolishes the association of FcαRI with the FcRγ chain (LAUNAY and al., 1999, aforementioned; MORTON and al., J. Biol. Chem. 270: 29781-29787, 1995).

The R209L/γ$_{chimera}$ construct results from the fusion of the extracellular and R209L transmembrane domains of FcαRI$_{R209L}$ to the intracytoplasmic tail of the human FcRγ chain.

The R209L/γ$_{chimera}$ was generated as follows. The extracellular and transmembrane domains of the R209L mutant were amplified by PCR using primers F$_{wt}$: GGGCTCGAGATGGACCCCAAACAGACCACC (SEQ ID NO: 1) and R$_{γ-α}$: CTTTCGCACTTGGATCTTCAGATTTTCAACCAGTATGGCCAA (SEQ ID NO: 2), as well as the intracellular domain of human FcαR γ-chain using primers F$_{α-γ}$: TTGGCCATACTGGTTGAAAATCTGAAGATCCAAGTGCGAAAG (SEQ ID NO: 3) and R$_γ$: GGGGGATCCTTACTGTGGTGGTTTCTCATG (SEQ ID NO: 4). PCR products were fused by overlapping extension PCR.

Figure 4:
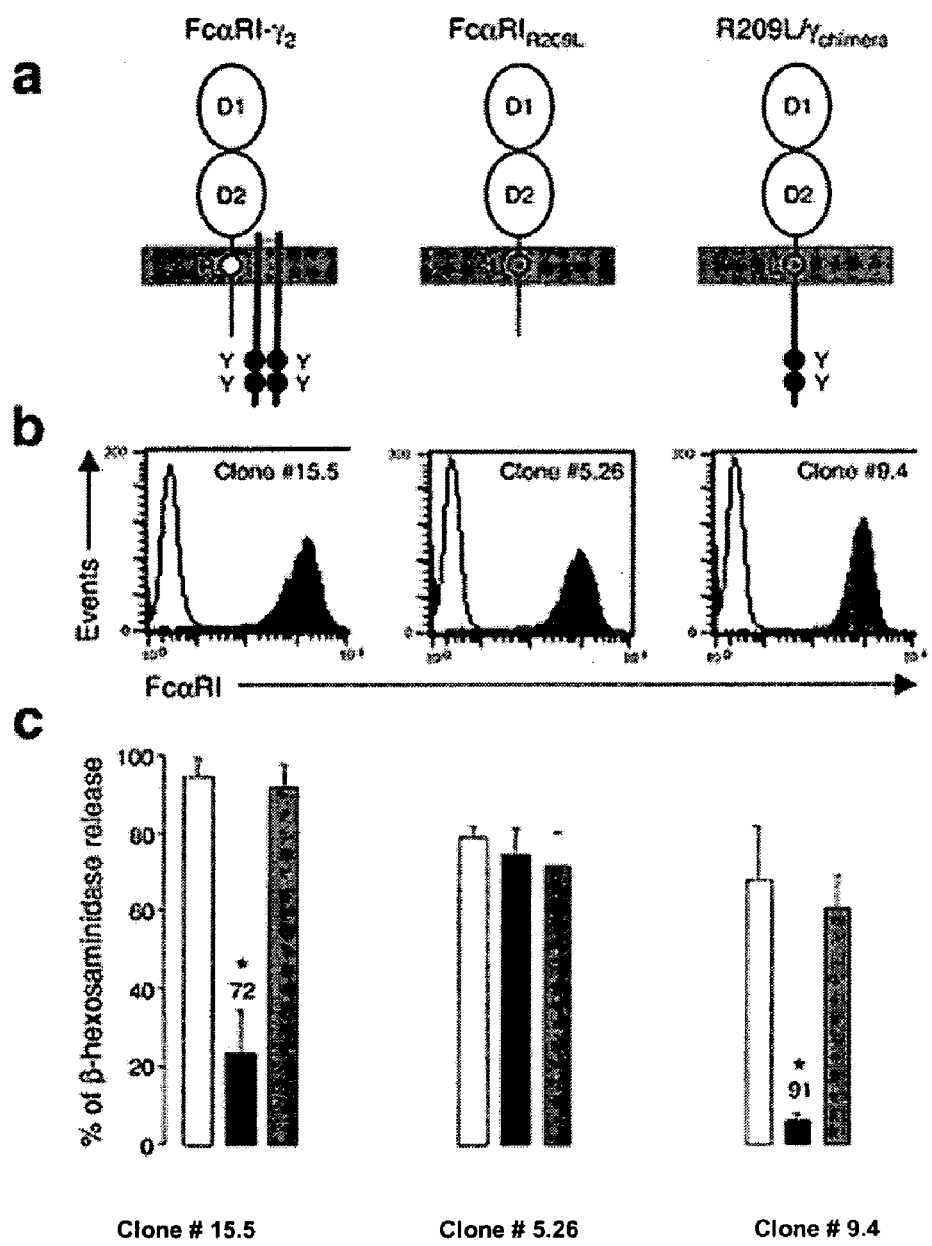
FIG. 4(a) illustrates schematic representations of the structures of the FcαRI-Y$_2$ receptor, the FcαRI$_{R209L}$ receptor and the R209L/Y$_{chimera}$ receptor.
FIG. 4(b) illustrates the results of a determination of FcaRI expression by flow cytometry. The results showed that all RBL-2H3 transfectants expressed significant levels of FcαRI at the cell surface.
FIG. 4(c) illustrates the results of testing the degranulation response of three transfectant clones. The numbers above the bars indicate the percentage of inhibition as compared to an irrelevant control Fab. The legend for this figure is described at Example 4.

The structures of the wild type FcαRI-γ$_2$ receptor, of the FcαRI$_{R209L}$ receptor, and of the R209L/γ$_{chimera}$ receptor are schematically represented in FIG. 4a.

All constructs were cloned into pSRαNeo vector and transfected in RBL-2H3 cells, as described in Example 2.

Cells transfected with wild-type human FcαRI (clone 15.5), FcαRI-γ$_2$ (clone 5.26) or R209L/γ$_{chimera}$ (clone 9.4) construct were selected.

The results of determination of FcαRI expression by flow cytometry are shown in FIG. 4b. These results show that all RBL-2H3 transfectants expressed significant levels of FcαRI at the cell surface.

The degranulation response was tested as described in Example 2 2).

The results are shown in FIG. 4c.
Legend of FIG. 4c:
□=IgE
■=IgE+irrelevant Fab 320
▨=IgE+anti-FcαRI Fab A77
* P<0.02, Student's unpaired t test
Numbers above the bars indicate the percentage of inhibition as compared to an irrelevant control Fab.

The results show that all transfectants sensitised with IgE alone exhibited over 50% FcεRI-mediated degranulation. Anti-FcαRI Fab A77 treatment was non inhibitory in RBL-2H3 transfected with the R209L mutant (clone 5.26) indicating that the intracellular tail of FcαRI did not contain the motif responsible for the inhibitory signaling. In contrast, the binding of anti-FcαRI Fab A77 to the FcαRI$_{R209L}$/γ chimeric receptor in transfected cells (clone 9.4) restored the inhibitory effect on degranulation to an extent similar to that observed in cells transfected with the wild type receptor (clone 15.5)

(91% and 72%, respectively). Similar results were obtained with at least three additional clones for each type of transfectants (not shown).

Aggregation of this FcαRI$_{R209L}$/γ chimeric receptor induced degranulation, demonstrating that, like wild-type FcαRI, it was able to mediate both activation and inhibition (not shown).

As the FcRγ chain does not bear any known inhibitory motif, the FcRγ ITAM usually known as an activatory motif was investigated to know whether it could also mediate the inhibitory effect. The human FcRγ chain contains two carboxy-terminal tyrosines (Y268 and Y278 within the FcαRI$_{R209L}$/γ chimeric receptor) being part of the ITAM motif known to play a role in cellular activation (17,24). Point mutations (Y268F, Y278F and double Y268/278F) were introduced in ITAM motif of the FcαRI$_{R209L}$/γ$_{chimera}$.

Stable transfectants (simple or double) established in RBL-2H3 cells transfected with the R209L/γ$_{chimera}$ containing Y268F and/or Y278F mutations within ITAM motif were no longer able to mediate the inhibitory and the activatory response (not shown).

EXAMPLE 5

The FcαRI Inhibitory Signal Induces Tyrosine Phosphorylation and Affects Ca$^{2+}$ Influx A) Tyrosine Phosphorylation Assay Since ITAM-mediated signalling involves the activation of tyrosine kinases, monomeric targeting of the FcαRI/γ complex was investigated to know whether it involved tyrosine phosphorylation.

Indicated RBL transfectants (FcαRI-γ2, FcαRI$_{R209L}$/β$_{chimera}$ wild type, FcαRI$_{R209L}$/γ$_{chimera}$ Y268F/Y278F) were stimulated for 15 min with 10 μg/ml anti-FcαRI Fab A77, irrelevant Fab 320, 40 μg/ml RAM F(ab')$_2$ or a combination of anti-FcαRI A77 F(ab')$_2$ plus RAM F(ab')$_2$.

After stimulation and two washes in ice-cold PBS, cells were solubilized in lysis buffer (50 mM HEPES pH 7.4, 1% Triton X-100, 0.1% SDS, 50 mM NaF, 50 mM NaCl, 1 mM Na$_3$VO$_4$, 30 mM Na$_4$P$_2$O$_7$, 50 U/ml aprotinin, 10 μg/ml leupeptin) and post-nuclear supernatants were prepared. Lysates were resolved by SDS—10% PAGE and proteins were transferred onto PVDF membrane. After blocking in 4% BSA, membranes were incubated with 4G10 anti-PY Ab (Upstate Biotechnology, Lake Placid, N.Y.) for 1 h at room temperature and with goat anti-mouse Ig coupled to HRP (Southern Biotechnology Associates, Birmingham, Ala.). Membranes were then striped and re-probed with anti-rat phospholipid scramblase (PLSCR) mAb (PASTORELLI and al., 2001, aforementioned) to evaluate equal loading. Filters were developed by ECL (Amersham-Pharmacia Biotech).

Figure 5:
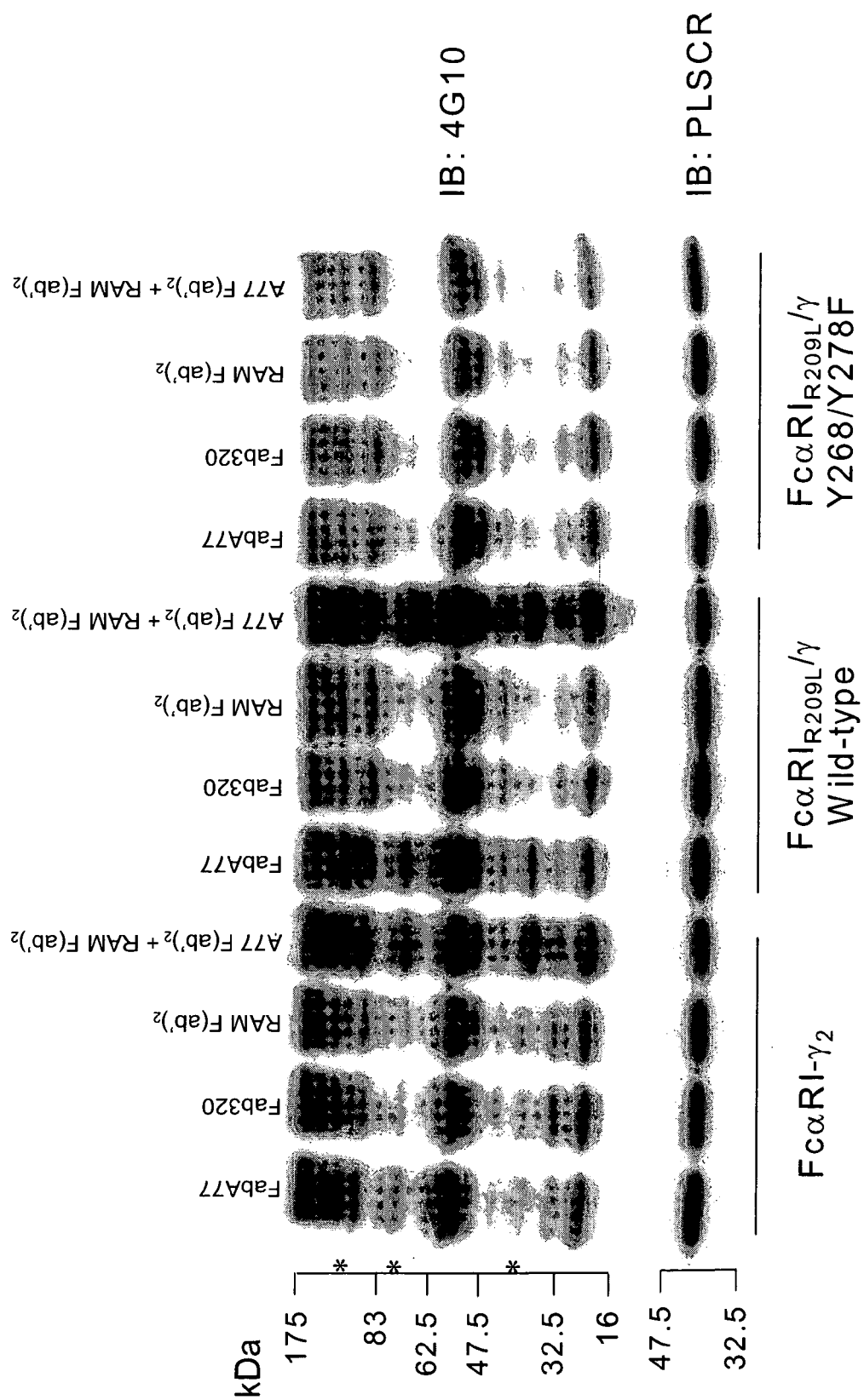
FIG. 5 illustrates the results of a tyrosine phosphorylation assay indicating prominent tyrosine phosphorylated proteins in stimulated cells. This shows that incubation of FcaRI transfectants with anti-FcaRI Fab A77 induced appearance of several tyrosine-phosphorylated proteins as compared to irrelevant control Fab. The legend for this figure is described at Example 4, section A).

The results are shown in FIG. 5.

Legend of FIG. 5:

* indicates prominent tyrosine phosphorylated proteins in stimulated cells.

The results show that incubation of FcαRI transfectants with anti-FcαRI Fab A77 induced appearance of several tyrosine-phosphorylated proteins as compared to irrelevant control Fab. The pattern of phosphoproteins appeared identical to the one obtained after multimeric aggregation of FcαRI, yet differed in its intensity. Similar data were obtained with the FcαRI$_{R209L}$/γ chimeric receptor, while mutations in ITAM abrogated the capacity of this receptor to initiate tyrosine phosphorylation after both monomeric and multimeric targeting.

B) Measurement of Cytosolic Calcium.

Modulation of the activatory steps was examined regarding effect of anti-FcαRI Fab A77 on the cytosolic calcium influx ([Ca$^{2+}$]$_i$), which is a key messenger for cell activation.

1) Experimental Protocol

Aliquots (1.5×10$^6$ cells) of human FcαRI transfectants, or of untransfected RBL-2H3 cells were sensitized with different test reagents (indicated hereafter for each experiment), in complete DMEM supplemented with 20 mM HEPES pH 7.6 during 1 h at 37° C. Cells were then loaded with 4 μM of the fluorescent probe FURA-2-AM (Molecular probes, Leiden, The Netherlands) for 30 min at 37° C.

After washing, cells were resuspended at 1×10$^6$ cells/ml in PBS containing 2 mM CaCl$_2$, 1 mM MgCl$_2$, 0.5 mg/ml gelatin and placed into a stirred and thermostated bowl. Cells were activated by the addition of 0.1 μg/ml DNP-HAS antigen (Ag) or 50 nM thapsigargin (Sigma). [Ca$^{2+}$]$_i$ was calculated using the computer software supplied with the spectrofluorimeter (Hitachi F 2000, Salem, N.H.) according to the formula given by GRYNKIEWICZ et al. (J. Biol. Chem. 260: 3440-3450, 1985). No significant cellular auto-fluorescence was observed, and the compounds used did not alter FURA-2-AM fluorescence. The contribution of intracellular stores was determined after stimulation in the presence of 3.5 mM EGTA. For fluorescence quenching studies, Mn$^{2+}$ (200 μM) was added to cells incubated in Ca$^{2+}$-free medium (BERTHON and al., Biochem. Pharmacol. 47: 789-794, 1994).

2) Inhibition of the Ca$^{2+}$ Plateau Phase by Anti-FcαRI Fab

Human FcαRI transfectants (a, clone 15.4) and untransfected RBL-2H3 cells (b) were sensitized with IgE alone or with IgE plus 10 μg/ml anti-FcαRI Fab A77 or irrelevant Fab 320.

Figure 6:
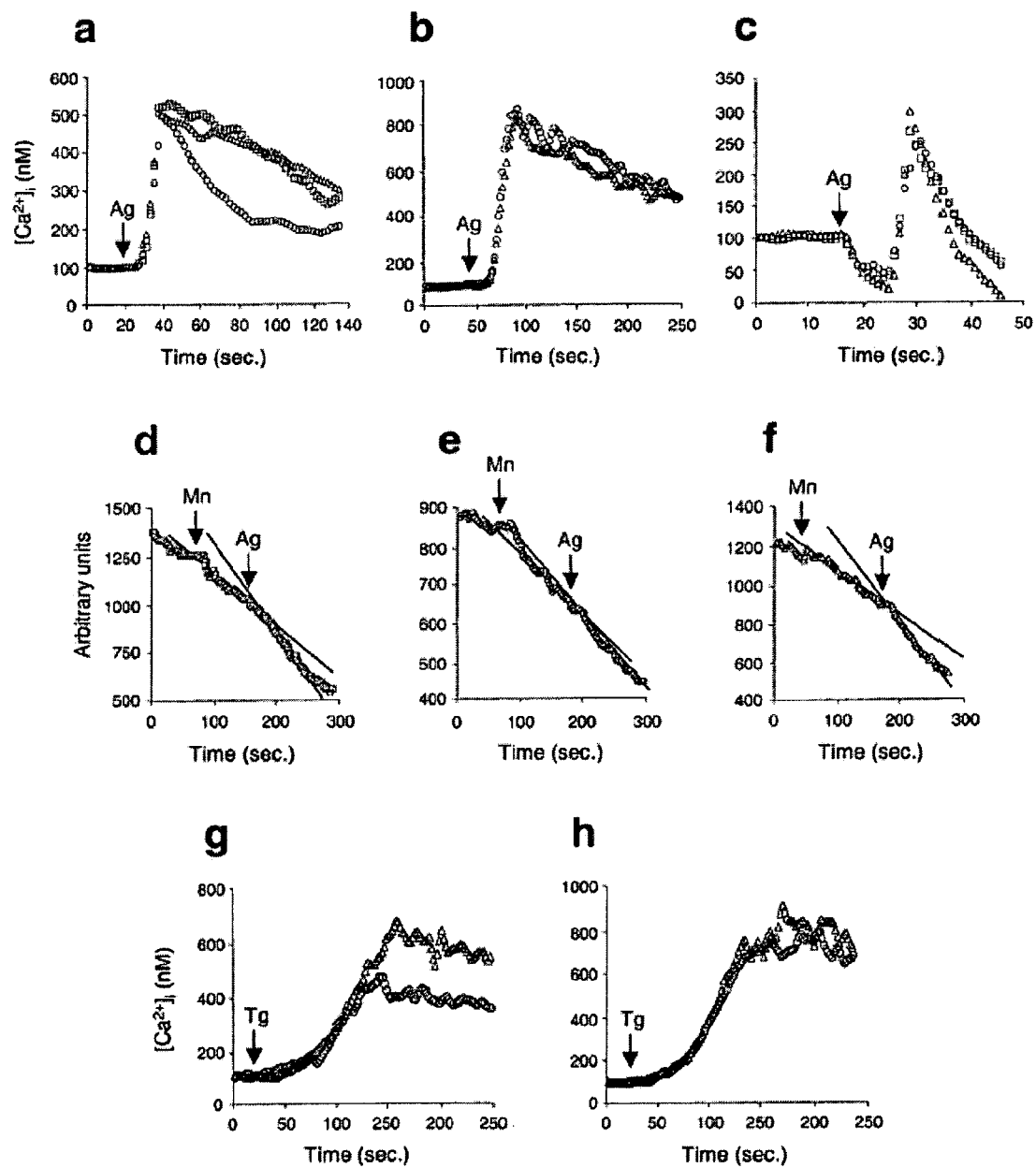
FIGS. 6(a,b) illustrate results of three experiments showing that the intracellular calcium peak after FcaRI stimulation was unaffected, but the plateau phase of elevated $[Ca^{2+}]_I$ was markedly inhibited after preincubation of FcaRI transfectants with anti-FcaRI Fab A77, as compared to an irrelevant control or non-transfected cells. The legend for this figure is described at Example 5, section 2).

The results are shown in FIGS. 6a and 6b.

Legend of FIGS. 6a and 6b:

a=Human FcαRI transfectants
b=untransfected RBL-2H3 cells
Ag: stimulation with DNP-HAS antigen
□=IgE alone
○=IgE+anti-FcαRI Fab A77
Δ=IgE+irrelevant Fab 320

Data are representative of at least three separate experiments.

The intracellular calcium peak after FcεRI stimulation was unaffected (FIG. 6a, □), but the plateau phase of elevated [Ca$^{2+}$]$_i$ was markedly inhibited after preincubation of FcαRI transfectants with anti-FcαRI Fab A77 (FIG. 6a, ○), as compared to an irrelevant control Fab (FIG. 6a, Δ) or non transfected cells (FIG. 6b).

3) Effect of Anti-FcαRI Fab on Release from Intracellular Ca$^{2+}$ Stores

Human FcαRI transfectants (clone 15.4) were sensitized with IgE alone or with IgE plus 10 μg/ml anti-FcαRI Fab A77 or irrelevant Fab 320. Cells were then loaded with FURA-2-AM as indicated and extracellular calcium was chelated with 3.5 mM EGTA shortly before determining [Ca$^{2+}$]$_i$ to discriminate between calcium release from intracellular stores and calcium entry from the external medium. The results are shown in FIG. 6c.

Legend of FIG. 6c:

Ag: stimulation with DNP-HAS antigen
□=IgE alone
○=IgE+anti-FcαRI Fab A77
Δ=IgE+irrelevant Fab 320

Data are representative of at least three separate experiments.

The results show that anti-FcαRI Fab A77 treatment had no effect on EGTA-treated cells indicating that it did not inhibit the release of intracellular calcium stores.

4) Anti-FcαRI Fab Inhibits $Ca^{2+}$ influx

To confirm that only calcium influx was affected, external $Ca^{2+}$ was replaced with $Mn^{2+}$, that enters cells through store-operated calcium channels (SOC) and competes with free internal calcium, thereby quenching FURA-2-AM fluorescence (BERTHON and al., 1994, aforementioned).

Human FcαRI transfectants (clone 15.4) were sensitized with IgE alone (d) or with IgE plus 10 µg/ml anti-FcαRI Fab A77 (e) or irrelevant Fab 320 (f).

The results are shown in FIGS. 6d-f.

Legend of FIGS. 6d-f:

Ag: stimulation with DNP-HAS antigen

Mn: addition of $Mn^{2+}$ d=IgE alone e=IgE+anti-FcαRI Fab A77 f=IgE+irrelevant Fab 320

Data are representative of at least three separate experiments. The results show that addition of $Mn^{2+}$ decreased fluorescence, owing spontaneous entry of $Mn^{2+}$ ions into cells. FcεRI stimulation induced a further significant decrease in fluorescence as a consequence of $Mn^{2+}$ influx through opened SOC (FIG. 6d). Cell incubation with anti-FcαRI A77 prior to IgE-dependent stimulation abrogated this effect (FIG. 6e), while an irrelevant Fab 320 was ineffective (FIG. 6f).

Ag induced FURA-2-AM fluorescence quenching, due to $Mn^{2+}$ influx, with slopes corresponding to calcium entry before and after stimulation are respectively of 2.5 and 4.1 (d), 1.8 and 1.9 (e), and 3.5 (f).

5) Anti-FcαRI Fab Inhibits Events Between Calcium Release from Internal Stores and the Opening of SOC To investigate whether FcαRI-mediated inhibition targeted events between calcium release from internal stores and calcium influx, thapsigargin was used, a pharmacologic agent that depletes inositol triphosphate-sensitive stores, resulting in SOC opening, in the absence of transmembrane receptor engagement (THASTRUP and al., Agents Actions 27: 17-23, 1989).

Human FcαRI transfectants (clone 15.4) (g) and untransfected RBL-2H3 cells (h) were sensitized with 10 µg/ml anti-FcαRI Fab A77 or irrelevant Fab 320. After loading the cells with FURA-2-AM, $[Ca^{2+}]_i$ was measured following stimulation with 50 nM thapsigargin (Tg).

Data are representative of at least three separate experiments.

The results are shown in FIGS. 6g and 6h.

Legend of FIGS. 6g and 6h:

g=Human FcαRI transfectants h=untransfected RBL-2H3 cells

Tg: stimulation with thapsigargin

○=anti-FcαRI Fab A77

∆=irrelevant Fab 320

The results show that thapsigargin-induced sustained $[Ca^{2+}]_i$ elevation was markedly reduced by preincubation with anti-FcαRI Fab A77 in FcαRI-transfected cells, as compared to irrelevant Fab 320 or untransfected cells (FIG. 6h).

EXAMPLE 6

FcαRI Targeting Prevents IgE-Mediated Manifestations of Asthma In Vivo

The inhibitory activity of FcαRI being demonstrated in vitro, in vivo targeting of this receptor was tested to know whether it could inhibit inflammatory responses.

As mice do not express FcαRI homologs (KABAGAWA and al., Proc. Nat. Acad. Sci. 94: 5261-5266, 1997; HAYAMI and al., J. Biol. Chem. 272: 7320-7327, 1997), Balb/c transgenic mice (Tg) expressing the human FcαRI (CD89, line 83) under the control of the CD11b promoter were used, yielding myeloid cell expression similar to that observed in humans (LAUNAY and al., J. Exp. Med. 191: 1999-2009, 2000). Genotyping was done by PCR (LAUNAY and al., 2000, aforementioned). Mice were bred and maintained at the mouse facilities of IFR 02 and Bichat Medical School. All experiments were done in accordance with national guidelines.

Anti-FcαRI Fab immunotherapy was tested in an IgE-mediated animal model of asthma according to ZUBERI and al. (J. Immunol. 164: 2667-2673, 2000) which protocol was adapted. Briefly, FcαRI-transgenic Balb/c mice (Tg) and littermate controls (Lt) were immunized intraperitoneally twice with 10 µg TNP-OVA (Sigma) in 2 mg of aluminium hydroxide gel per 25 g body weight on days 0 and 7. Starting on day 14, mice were challenged intranasally daily for 7 consecutive days with PBS or 2 µg TNP-OVA complexed with 20 µg anti-DNP IgE (IC) in the presence of 5 µg anti-FcαRI Fab A77 or irrelevant Fab 320. On day 14, mice received 50 µg anti-FcαRI Fab A77 or control Fab intraperitoneally. Twelve hours after the final intranasal challenge, unrestrained conscious mice were placed in a whole-body plethysmograph chamber (BUXCO Electronics, Sharon, Conn.). After stabilization for a few minutes, an aerosol of 300 mM methacholine was delivered for 60 sec.

Changes in airway resistance was calculated every minute for 20 min after methacholine exposure, as follows: enhanced pause (Penh)=[(expiratory time/relaxation time)−1]×(peak expiratory flow/peak inspiratory flow) (ZUANY-AMORIM and al., Science 280: 1265-1267, 1998).

Figure 7:
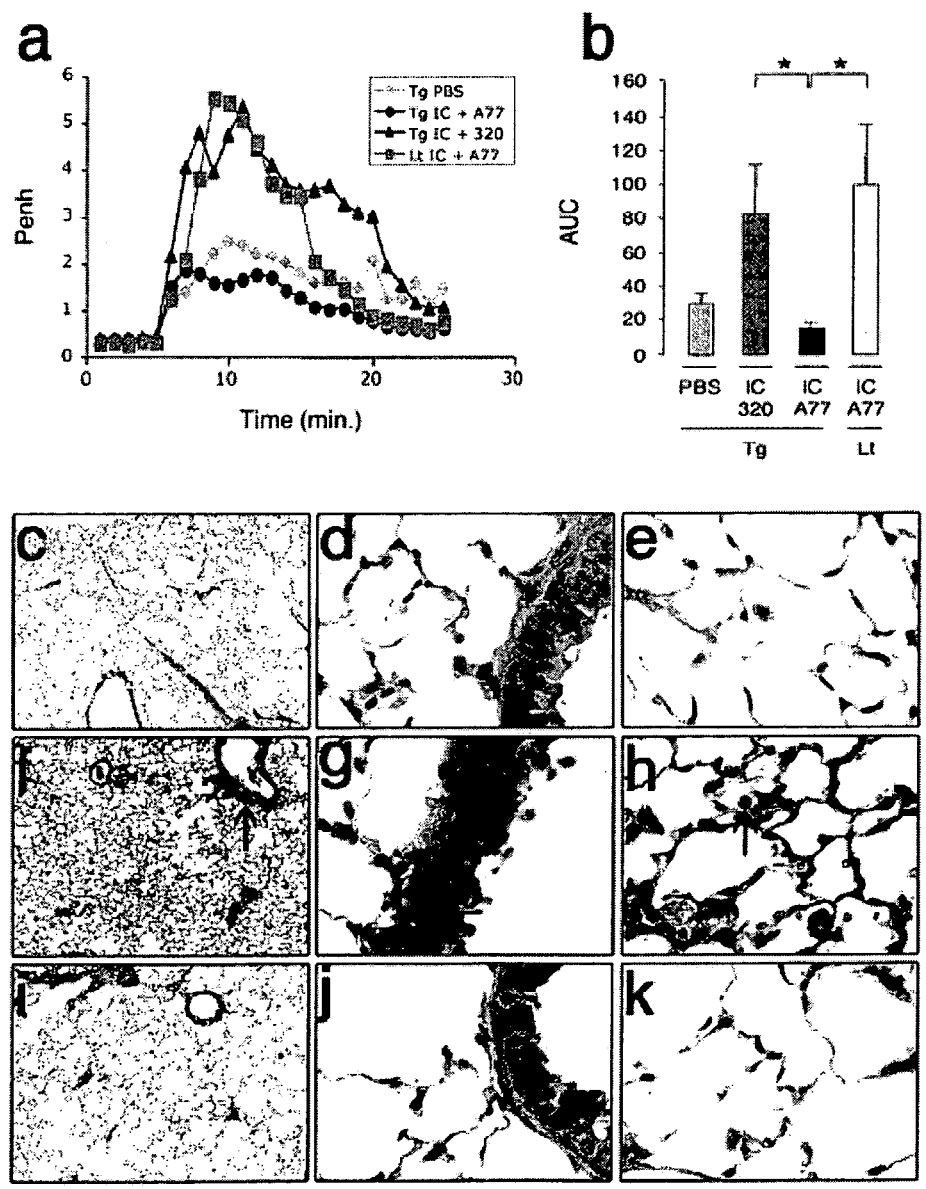
FIGS. 7 (a,b) illustrate that after repeated intranasal challenge with IgE immune complexes in the presence of an irrelevant Fab (FcαRI $^+$) Tg mice developed bronchial hyperactivity to inhaled methacholine, as compared to PBS-challenged counterparts. This phenomenon was abrogated by treating transgenic mice with anti-FcαRI Fab. Bronchial hyperactivity was not reduced by anti-(FCαRI $^-$)Littermates control non-transgenic. The legend for these figures is described in Example 6.

The results are shown in FIG. 7a.

Legend of FIG. 7a:

◇=Tg PBS

●=Tg IC+anti-FcαRI Fab A77

∆=Tg IC+irrelevant Fab 320

▨=Lt IC+anti-FcαRI Fab A77

Curves represent mean aiway resistance.

Cumulative areas under the curve (AUC), of corresponding Penh values were means ±SD of three distinct experiments involving at least eight mice per group, and were represented graphically.

The results are shown in FIG. 7b.

Legend of FIG. 7b:

□=Tg PBS

▨=Tg IC+irrelevant Fab 320

■=Tg IC+anti-FcαRI Fab A77

□=Lt IC+anti-FcαRI Fab A77

* P<0.05, Student's unpaired t test.

The results show that after repeated intranasal challenge with IgE immune complexes in the presence of an irrelevant Fab, (FcαRI+) Tg mice developed bronchial hyperactivity to inhaled methacholine, as compared to PBS-challenged counterparts (FIGS. 7a, 7b). This phenomenon was abrogated by treating transgenic mice with anti-FcαRI Fab (FIGS. 7a, 7b). Bronchial hyperactivity was not reduced by anti-FcαRI Fab in (FcαRI−) Littermates control non-transgenic (FIGS. 7a, 7b).

A morphological analysis of lung tissue sections from FcαRI-transgenic mice was done. Animals were anaesthetized; lungs were inflated by tracheal injection of 1 ml of Optimum Cutter temperature Compound (BDH, Poole, United Kingdom), fixed in 4% paraformaldehyde, dehydrated in graded alcohols, and embedded in paraffin. Comparative histopathologic evaluation of the degree of inflammation was performed on entire H&E-stained lung sections.

The results are shown in FIGS. 7c-k

Legend of FIGS. 7c-k:

c-e=control PBS-challenged mice f-h=antigen-challenged mice treated with irrelevant Fab 320 i-k=antigen-challenged mice treated with anti-FcαRI Fab A77

Magnification ×10 (c,f,i), ×100 (d,e,g,h,j,k)

Pulmonary histology of antigen-challenged Tg mice treated with the irrelevant Fab 320 showed peribronchial (FIG. 7f) and epithelial (FIG. 7g) inflammatory infiltrates consisting mainly of granulocytes and mononuclear cells, and diffuse alveolar capillary congestion (FIG. 7h) (see arrows). These features were absent in lungs from PBS-challenged mice (FIGS. 7c-e) showing normal physiology. Antigen-challenged anti-FcαRI Fab A77-treated mice showed substantially less inflammation and congestion (FIGS. 7i-k). Anti-FcαRI Fab administration prevented antigen-induced airway congestion and infiltration by inflammatory cells.

No effects were observed in the lungs of (FcαRI−) littermates treated with anti-FcαRI Fab (not shown).

EXAMPLE 7

Effects of FcαRI Targeting on Non-Immune Renal Inflammation

Anti-FcαRI immunotherapy was also tested after unilateral ureteral obstruction (UUO) in mice, an inflammatory model of interstitial renal fibrosis and obstructive nephropathy (KLAHR and MORRISSEY, Am. J. Physiol. Renal Physiol. 283(5): F861-875, 2002). The kidneys are characterized by tubular dilatation, infiltration of inflammatory cells such as macrophages, and epithelial-mesenchymal transition of the kidney. Briefly, unilateral obstruction or the ureter of the left kidney was performed on anaesthetized Tg CD89 mice by ligation at two locations. One day before and daily after chirurgical intervention, mice were treated with either PBS, 100 μg irrelevant Fab 320 or 100 μg Fab A77. On day 6, mice were sacrificed and obstructed kidney was processed for hispathologic evaluation (Periodic Acid Schiff (PAS) staining and immunohistochemical staining with anti-CD11b antibody).

Figure 8:
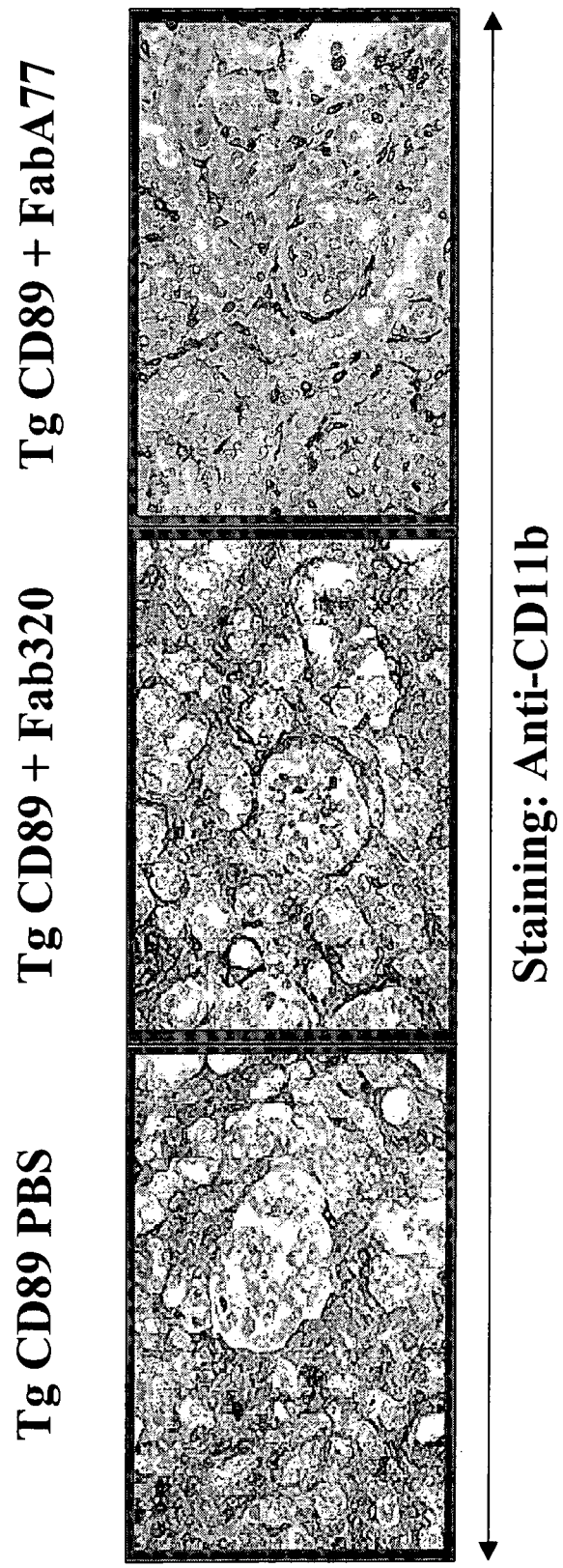
FIG. 8 illustrates that PBS-treated kidneys show typical pathological features of UUO with dilated tubules and cellular infiltration, notably macrophages. These typical pathological features were almost absent in Fab A77-treated kidneys and cellular infiltration is considerably decreased. No effects were observed in the kidneys of the Fab 320-treated Tg CD89 mice. The legend for this figure is described in Example 7.

The results are shown in FIG. 8.

Legend of FIG. 8:

Tg CD89 PBS=obstructed kidneys of Tg CD89 mice treated with PBS

Tg CD89+Fab 320=obstructed kidneys of Tg CD89 mice treated with irrelevant Fab 320

Tg CD89+Fab A77=obstructed kidneys of Tg CD89 mice treated with Fab A77

The PBS-treated kidneys show typical pathologic features of UUO with dilated tubules and cellular infiltration (PAS staining, not shown), notably macrophages (anti-CD11b staining). These typical pathologic features were almost absent in Fab A77-treated kidneys and cellular infiltration is considerably decreased. No effects were observed in the kidneys of the Fab 320-treated Tg CD89 mice.

The invention claimed is:

1. A method of treating an inflammatory disease in a mammal, which comprises administering to the mammal an anti-inflammatory agent consisting of a monovalent antigen-binding fragment of an antibody directed against the EC2 domain of the FcαRI receptor.

2. The method of claim 1, wherein the inflammatory disease is selected from the group consisting of lupus, rheumatoid arthritis, diabetes, nephritis renal fibrosis, obstructive nephropathy and gut inflammatory disorders.

3. The method of claim 1, wherein the inflammatory disease is an allergy.

4. The method of claim 3, wherein the allergy is asthma.

5. The method of claim 1, whereby IgG-induced phagocytosis is inhibited.

6. The method of claim 5, whereby IgE-mediated exocytosis is further inhibited.

7. The method of claim 4, whereby antigen-induced bronchial hyper-reactivity is reduced.

8. The method of claim 1, wherein the monovalent antibody fragments are administered in a form of a composition.

9. The method of claim 8, wherein the composition is administered by injection.

10. The method of claim 9, wherein the injection is intramuscular, intradermal, intravenous, intraperitoneal or subcutaneous.

11. The method of claim 8, wherein the composition is administered by aerosol.

12. The method of claim 1, wherein the mammal is human.

13. The method of claim 1, wherein the antibody fragments are Fab fragments of an anti-FcαRI mAb.

14. The method of claim 13, wherein the anti-FcαRI mAb is (IgG1k, clone A 77).

* * * * *